(12) United States Patent
Levin et al.

(10) Patent No.: US 9,311,449 B2
(45) Date of Patent: Apr. 12, 2016

(54) HOSPITAL UNIT DEMAND FORECASTING TOOL

(75) Inventors: Scott R. Levin, Baltimore, MD (US);
Scott Zeger, Baltimore, MD (US);
Melissa McCarthy, Baltimore, MD (US); Jim Fackler, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 317 days.

(21) Appl. No.: 14/117,884

(22) PCT Filed: May 17, 2012

(86) PCT No.: PCT/US2012/038266
§ 371 (c)(1),
(2), (4) Date: Jan. 28, 2014

(87) PCT Pub. No.: WO2012/158871
PCT Pub. Date: Nov. 22, 2012

(65) Prior Publication Data
US 2014/0136458 A1 May 15, 2014

Related U.S. Application Data

(60) Provisional application No. 61/487,183, filed on May 17, 2011.

(51) Int. Cl.
*G06F 15/18* (2006.01)
*G06E 1/00* (2006.01)
*G06E 3/00* (2006.01)
*G06G 7/00* (2006.01)
(Continued)

(52) U.S. Cl.
CPC ............ *G06F 19/345* (2013.01); *G06N 3/0427* (2013.01); *G06Q 10/06312* (2013.01)

(58) Field of Classification Search
None
See application file for complete search history.

(56) References Cited

U.S. PATENT DOCUMENTS 5,809,477 A 9/1998 Pollack
7,248,159 B2 * 7/2007 Smith .................... G08B 21/10
128/903

(Continued)

OTHER PUBLICATIONS

Inference of a continuous auto-regressive model for the forecasting of nonstationary stochastic processes deriving from energy demand in electrical networks Cavallini, A.; Mazzanti, G.; Montanari, G.C. Electrotechnical Conference, 1996. MELECON '96., 8th Mediterranean Yr:1996, vol. 2 pp. 726-729 vol. 2, DOI: 10.1109/MELCON.1996.551320.*

(Continued)

*Primary Examiner* — Michael B Holmes
(74) *Attorney, Agent, or Firm* — Johns Hopkins Technology Ventures

(57) ABSTRACT

An embodiment in accordance with the present invention provides a method of forecasting a demand for a particular hospital unit. The method can be executed by programming the steps into a computer readable medium. One step includes logging a total number of beds in the particular hospital unit and available nursing slots to determine a capacity for the particular hospital unit. The method also includes analyzing data for patients scheduled to stay in the particular hospital unit data to predict stochastic arrivals in order to estimate a total inflow. A length of stay of a patient in the particular hospital unit is predicted using a survival analysis based on physician orders to estimate a total outflow. Additionally, the method includes executing an algorithm designed to use the capacity, total inflow, and total outflow to determine the demand for the particular hospital unit.

20 Claims, 11 Drawing Sheets

(51) Int. Cl.
*G06F 19/00* (2011.01)
*G06Q 10/06* (2012.01)
*G06N 3/04* (2006.01)

(56) References Cited

U.S. PATENT DOCUMENTS

| | | | | |
|---|---|---|---|---|
| 7,411,493 B2 * | 8/2008 | Smith | ...................... | H04W 4/02 340/539.11 |
| 2004/0243438 A1 * | 12/2004 | Mintz | .................... | G06Q 10/04 705/2 |
| 2005/0197775 A1 * | 9/2005 | Smith | .................... | G08B 21/10 702/3 |
| 2005/0240378 A1 * | 10/2005 | Smith | .................... | G08B 21/10 702/188 |
| 2006/0015254 A1 * | 1/2006 | Smith | .................... | H04W 4/02 702/3 |
| 2007/0296574 A1 * | 12/2007 | Smith | .................... | G08B 21/10 340/539.13 |
| 2010/0198609 A1 | 8/2010 | Mellin et al. | | |
| 2012/0136671 A1 * | 5/2012 | Alt | ........................ | G06F 19/327 705/2 |
| 2014/0136458 A1 * | 5/2014 | Levin | ............... | G06Q 10/063 12 706/21 |
| 2014/0297302 A1 * | 10/2014 | Vanier | .................. | G06F 19/322 705/2 |

OTHER PUBLICATIONS

Comparison between Nearest Neighbours and Bayesian Network for demand forecasting in supply chain management Gaur, M.; Goel, S.; Jain, E. Computing for Sustainable Global Development (INDIACom), 2015 2nd International Conference on Year: 2015 pp. 1433-1436 Referenced in: IEEE Conference Publications.*

Analysis and prediction of the total number of ice-snow tourism in Heilongjiang based on times series: A case study of Harbin Xu Yijun; Yu Zhang Robotics and Applications (ISRA), 2012 IEEE Symposium on Year: 2012 pp. 624-626, DOI: 10.1109/ISRA.2012.6219266 Referenced in: IEEE Conference Publications.*

Evolutionary Optimal Virtual Machine Placement and Demand Forecaster for Cloud Computing Mark, C.C.T.; Niyato, D.; Tham Chen-Khong Advanced Information Networking and Applications (AINA), 2011 IEEE International Conference on Year: 2011 pp. 348-355, DOI: 10.1109/AINA.2011.50 Referenced in: IEEE Conference Publications.*

Houdenhoven, M., et al., "Optimizing intensive care capacity using individual length-of-stay prediction models", Critical Care, (2007) vol. 11, Issue 2, pp. 1-10.

Ridge, J., et al., "Capacity planning for intensive care units", European Journal of Operational Research (1998), 105, pp. 346-355.

Nguyen, J., et al., "A universal method for determining intensive care unit bed requirements", Intensive Care Med (2003), 29:849-852.

McManus, M., et al., "Queuing theory accurately models the need for critical care resources", Anesthesiology (2004), vol. 100, No. 5, pp. 1271-1276.

Anand, K., et al., "Statistical models to predict the need for postoperative intensive care and hospitalization in pediatric surgical patients", Intensive Care Med (2001) 27:873-883.

* cited by examiner

HOSPITAL UNIT DEMAND FORECASTING TOOL

CROSS-REFERENCE TO RELATED APPLICATIONS

This application is a 35 U.S.C. §371 U.S. national entry of International Application PCT/US2012/038266 having an international filing date of May 17, 2012, which claims the benefit of U.S. Provisional Application No. 61/487,183 filed May 17, 2011, the content of each of the aforementioned applications is herein incorporated by reference in their entirety.

GOVERNMENT SUPPORT

This invention was made with government support under Systems and Engineering Design Program No. NSF 0927207 awarded by the National Science Foundation. The government has certain rights in the invention.

FIELD OF THE INVENTION

The present invention relates generally to hospital management. More particularly, the present invention relates to a method for estimating demand for a hospital unit.

BACKGROUND OF THE INVENTION

Economic pressure from health care reform paired with steady increases in demand for hospital services are forcing hospitals to do more with less. This places emphasis on efficiently managing all resources used to care for patients throughout their hospital stay. This includes effectively managing patient flow by minimizing patient waiting (i.e., non-value added time), reducing patients' length-of-stay and consequently improving patient access. There are several challenges to managing patient flow through an individual unit or entire hospital, and these challenges mainly stem from uncertainty (i.e., stochastic variability) in the demand for services over time.

A Pediatric Intensive Care Unit (PICU) is a specialized hospital unit or facility designed to treat children with a wide variety of life-threatening illnesses or injuries. A significant portion of PICU admissions are from trauma-related injuries which are a leading cause of death among children in the United States. Severely ill and injured children treated in large tertiary care PICUs have significantly better survival rates compared to children treated in non-tertiary care facilities. Improved outcomes associated with PICU care have been attributed to specialized services and staff (e.g., intensivists) and their increased use of advanced technologies and therapeutic modalities. Despite the benefits of tertiary PICUs, access remains poor. PICU facilities, which are only available in 9% of United States counties, have been disproportionally affected by the on-going nursing shortage further limiting access. Thus, it is critical that each PICU across the country operate efficiently, optimize scarce nursing resources, and provide timely care when children are in need.

Individual PICUs must manage patient flow efficiently to balance competing interests of providing consistently accessible services and maintaining financial viability (i.e., avoiding idle resources). Challenges arise from uncertainty and complexity caused by; (1) stochastic variability in demand for resources, (2) nurse staffing constraints, and (3) deficiencies in communication and coordination across the hospital system. An exemplary PICU rejects 20% of patient referrals, transfers out 14% of emergency patients and operates at only 77% average bed occupancy.

While many children within the hospital system are not rejected, they do experience delays in obtaining access. Pediatric surgery patients held post-surgery create Operating Room (OR) delays. Delays are common and inconvenience the patient, surgical team and incur heavy costs for OR idle time and staff overtime. Surgeries may be cancelled if it is anticipated that PICU resources are unavailable, however this is a rare occurrence (<2%). Children in the ED have prolonged stays and treatment areas are not always optimal. Delays in the ED for critically ill adults have been demonstrated to impact the progression of organ failure and significantly increase mortality rate. Children being treated in other children's hospital inpatient units (i.e., floors) may experience deterioration in clinical condition, requiring critical care services.

When PICU access is blocked, these patients must wait in their current units. Occasionally, children are forced to wait overnight in each of these sub-optimal care areas. Blocking PICU admissions obstructs patient flow at various locations within the children's hospital system. Conversely, congestion within the hospital impedes flow through the PICU. The majority of patients (84%) are transferred to other units within the hospital to receive lower levels of care before being discharged. A common barrier to transferring patients out is lack of available beds in downstream units. These patients awaiting transition consume valuable PICU resources that are likely to be more beneficial to patients awaiting access or patients turned away.

Daily PICU management functions involve; (1) ensuring appropriate staffing levels, (2) ensuring that patient needs for equipment and services are met, (3) decisions to accept/reject direct admits, (3) decisions to transfer ED patients to other facilities, and (4) decisions to cancel surgeries. Each of these functions necessitates projecting bed census at future times.

The proven benefits of pediatric critical care have led to increases in demand and subspecialty expansion. Nationwide increases in demand are possibly due to the rise in the number of children surviving from injuries or chronic illness as a result of advances in medicine. Expansion has partially resulted from a shift in pediatric bed distribution toward more high acuity PICU beds and fewer floor beds. However, the effects of capacity expansion have been mitigated by the on-going nursing shortage, which is expected to worsen. PICUs have been disproportionally effected by the rapid decline of young nurses (i.e., under age of 30) who are historically attracted to intensive care work.

An exemplary PICU has 26 beds and admits ~1650 patients annually with, 39% coming from operating rooms (OR), 26% from the pediatric emergency department (ED), 18% from children's hospital unit transfers, and 17% from referrals from external health care facilities (i.e., direct admits). Most PICU arrivals from the OR (97%) are selectively scheduled weeks in advance. Thus, OR patients are considered deterministic arrivals (i.e., known prior to 72 hours in advance). Patients admitted from other sources (61%) arrive naturally (i.e., unknown) and are considered stochastic. Stochastic arrivals from external health care facilities (i.e., direct admits) and the ED may be rejected. The PICU currently rejects 20% of direct admits and transports 14% of critically ill ED patients to other facilities because of lack of available resources.

Delays in the ED for critically ill adults have been demonstrated to impact the progression of organ failure and significantly increase mortality rate. These children may also be transported to external health care facilities, if PICU resources are unavailable. This is undesirable because it delays care, inconveniences the child and family, and incurs transportation costs. Children being treated in other children's hospital inpatient units (i.e., floors) may experience deterioration in clinical condition, requiring critical care services. When PICU access is blocked, these patients must wait in their current units. Occasionally, children are forced to wait overnight in each of these sub-optimal care areas. Blocking PICU admissions obstructs patient flow at various locations within the children's hospital system. Conversely, congestion within the hospital impedes flow through the PICU. The majority of patients (84%) are transferred to other units within the hospital to receive lower levels of care before being discharged. A common barrier to transferring patients out is lack of available beds in downstream units. These patients awaiting transition consume valuable PICU resources that are likely to be more beneficial to patients awaiting access or patients turned away.

Currently, nursing and bed projections are made using human intuition supplemented by standard status reports of PICU census and daily OR schedule, available each morning. Accurate projections are difficult in the stochastically variable PICU environment where the average patient census is 20 (i.e., 77% occupancy) with a 95% confidence interval of 13 to 25 children over 1-year. In addition, lack of updated PICU patient information and system component information further challenge managers' ability to project.

Models forecasting occupancy, patient arrivals, discharges, and other unit specific operational metrics have been developed for EDs and entire hospitals. Methods used within these studies include several variations of; autoregressive moving average (ARMA) models, exponential smoothing models, Poisson regression models, neural network models and discrete event simulation models. Models used to predict occupancy either use an ARMA type model on occupancy data or develop a structured model of components to forecast inflow (i.e., arrivals) and outflow (i.e., length-of-stay) independently. However, this assumption of independence may be flawed.

Inflow models employ a single above mentioned method to model arrival counts at discrete time intervals. Outflow models are most commonly comprised of length-of-stay prediction models; however there has been application of a model to predict discharge counts over discrete time intervals. Members of the proposed research team have applied several survival analysis methods to predict patient length-of-stay as function of patient, hospital, and environmental factors. Developing a forecasting model that is applicable in real-time poses a different set of intellectual and practical challenges, which have been addressed by only two previous studies. One study developed a discrete event simulation model to forecast measures of ED crowding and performed a prospective, real-time evaluation recently accepted for publication. Another study, describes an occupancy forecasting model for an entire hospital comprised of inflow and outflow components.

It would therefore be advantageous to provide a tool to forecast demand for hospital services that has the ability to inform decision making, optimize scarce resources and improve access.

SUMMARY OF THE INVENTION

The foregoing needs are met, to a great extent, by the present invention, wherein in one aspect a method of forecasting a demand for a particular hospital unit includes programming a computer readable medium with steps including the following. One step includes logging a total number of beds in the particular hospital unit and available nursing slots to determine a capacity for the particular hospital unit. The method also includes analyzing data for patients scheduled to stay in the particular hospital unit data to predict stochastic arrivals in order to estimate a total inflow. A length of stay of a patient in the particular hospital unit is predicted using a survival analysis based on physician orders to estimate a total outflow. Additionally, the method includes executing an algorithm designed to use the capacity, total inflow, and total outflow to determine the demand for the particular hospital unit.

In accordance with another aspect of the invention, the method includes estimating total inflow by analyzing predictive data related to a time of the day for the demand for the particular hospital unit. Estimating total inflow can also include analyzing predictive data related to a season of a year for the demand for the particular hospital unit. Estimating total outflow can include analyzing predictive data related to the ages of patients currently staying in the particular hospital unit. Additionally, estimating total outflow can include analyzing predictive data related to a source of arrival of patients currently staying in the particular hospital unit, and analyzing predictive data related to a time of the day for determining the demand for the particular hospital unit.

In accordance with another aspect of the present invention, the demand for the particular hospital unit is determined in six hour intervals for a 72 hour period of time. The demand for the particular hospital unit can, therefore, be determined every six hours within the 72 hour period of time. Stochastic arrivals are predicted using a feedback mechanism whereby the probability of stochastic arrivals being admitted to the particular hospital unit is a function of difference between forecasted demand and available capacity. A Poisson regression can be used to model the relationship between arrival counts and predictor variables from a stochastic source. Survival analysis can be done using discrete-time logistic regression, semi-parametric hazard regression, or parametric unbiased, stable estimates.

In accordance with yet another aspect of the present invention, physician orders can be grouped as medication orders, breathing support orders, and feed orders, and physiological measures from the patient can be used as a predictor of length of stay. Available nursing slots are based on predictive data generated every 12 hours, and are updated every three hours based on trigger events. The length of stay is grouped as a short stay of less than three days or a long stay of more than three days. The demand for a particular hospital unit can be updated in real time. The particular hospital unit can be a Pediatric Intensive Care Unit or any other hospital unit known to one of skill in the art. Information representative of the demand for a particular hospital unit can be outputted for review by a practitioner or manager.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements and.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

An embodiment in accordance with the present invention provides a method of forecasting a demand for a particular hospital unit. The method can be executed by programming the steps into a computer readable medium. One step includes logging a total number of beds in the particular hospital unit and available nursing slots to determine a capacity for the particular hospital unit. The method also includes analyzing data for patients scheduled to stay in the particular hospital unit data to predict stochastic arrivals in order to estimate a total inflow. A length of stay of a patient in the particular hospital unit is predicted using a survival analysis based on physician orders to estimate a total outflow. Additionally, the method includes executing an algorithm designed to use the capacity, total inflow, and total outflow to determine the demand for the particular hospital unit.

While the invention is described with respect to a Pediatric intensive Care Unit (PICU), it should be noted that this exemplary hospital unit is not meant to be considered limiting, and the method can be applied to any hospital unit with a need for availability forecasting known to one of skill in the art.

Figure 1:
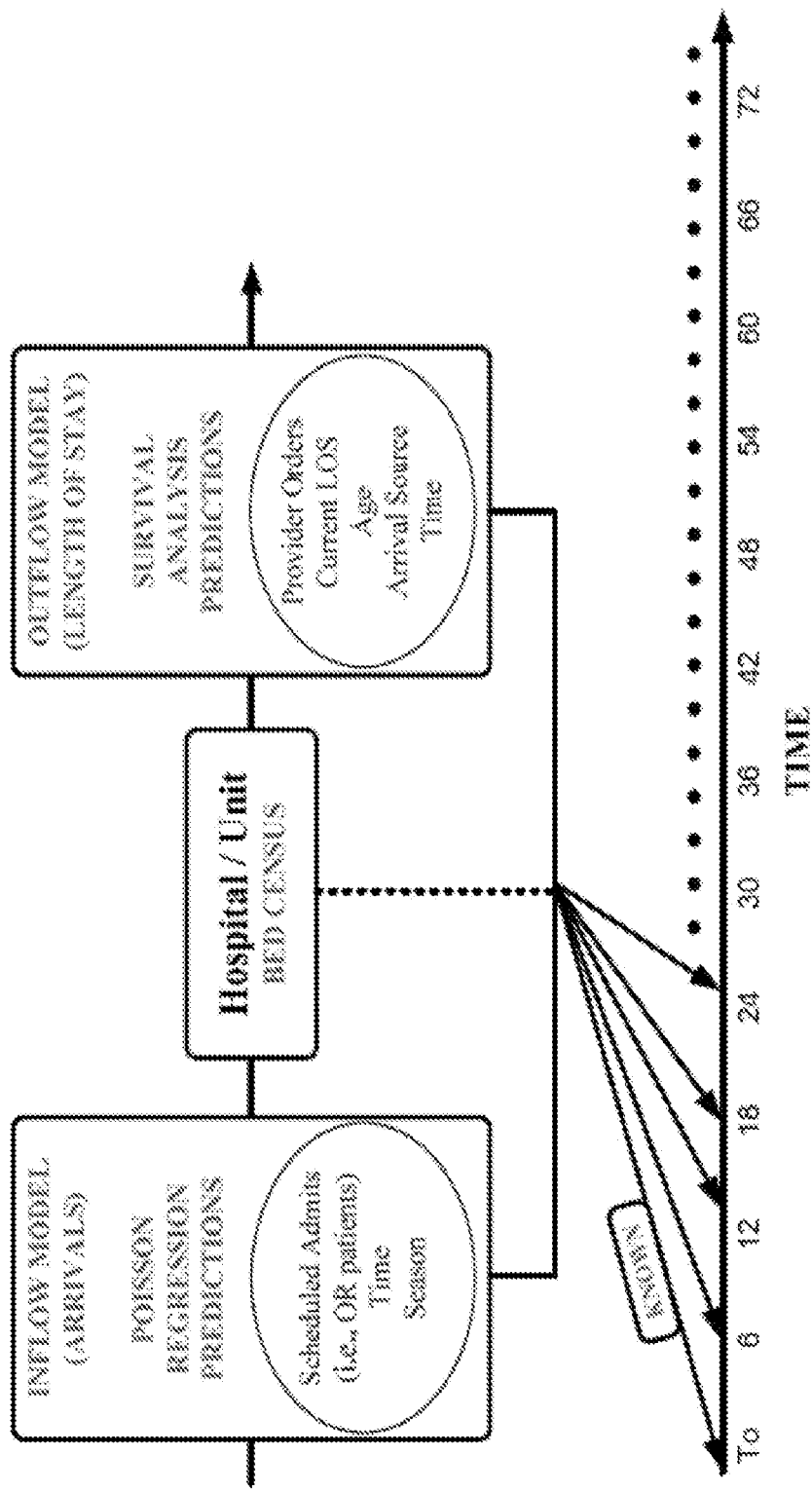
FIG. 1 illustrates a real-time resource demand forecasting tool according to an embodiment of the invention.

As illustrated in FIG. 1, the present invention includes a near real-time PICU resource demand forecasting model ('PICU-Forecast'). The model forecasts demand for nurse staffing and bed resources up to 72 hours into the future. PICU-Forecast has potential to; (1) improve daily decision making by reducing uncertainty in PICU system state projections, (2) improve coordination across the children's hospital system, and (3) facilitate proactive interventions to eliminate bottlenecks, avoid underutilization, and improve access.

Further, as illustrated in FIG. 1, PICU-Forecast is comprised of patient inflow and outflow models and uses retrospective data collected from multiple clinical information systems at the Johns Hopkins Children's Hospital. The method includes steps to execute the following: 1. Create an inflow model to predict stochastic (i.e., unscheduled) arrivals and corresponding probabilities of admission and nurse-to-patient ratios 2. Create an outflow model to predict PICU patient length-of-stay (i.e., discharge time) using survival analysis based on physician orders (i.e., medications, ventilation, etc.) 3. Integrate inflow and outflow models to create a global 'PICU-Forecast' model predicting PICU nursing and bed demand. This is achieved by transforming the temporal component of survival analysis from "study time" (i.e., patients' arrival times artificially aligned in time) to calendar time (i.e., using patients' actual arrival times). The probabilistic forecasting techniques proposed are applicable to modeling any dynamic sociotechnical flow system in real time.

The method can also be used to optimize scarce critical care resources to improve access and outcomes for children who are severely ill or injured. The forecasting methods, which will use readily available patient and hospital information to improve patient flow and optimize nursing resources, are potentially applicable to any hospital unit with capable information technology (i.e., most large tertiary-care medical facilities)

An accurate near real-time PICU resource demand forecasting model has potential to; (1) reduce uncertainty in PICU system state projections leading to improved daily decision-making, (2) improve coordination across the children's hospital system, and (3) facilitate proactive interventions to avoid bottlenecks and improve access to PICU services. The ultimate goal of the proposed research is to develop PICU-Forecast into a web-based information technology tool that may be used in clinical practice.

Figure 2:
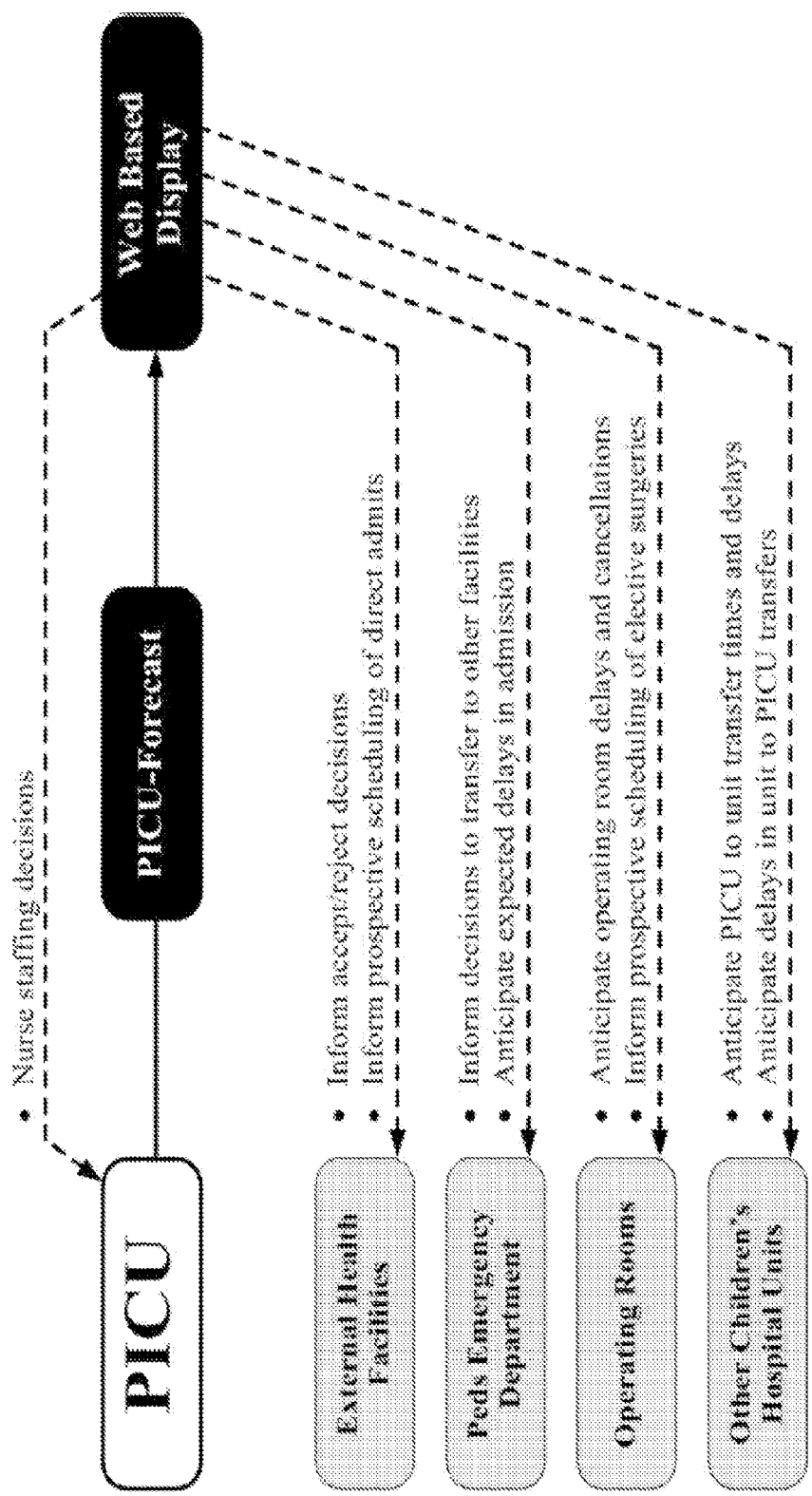
FIG. 2 illustrates a conceptual model of the use of a real-time resource demand forecasting tool according to an embodiment of the invention.

FIG. 2 illustrates a conceptual model of how information from PICU-Forecast would be used to reduce uncertainty, anticipate delays in care, and improve decision making across the children's hospital system. First, PICU-Forecast could be used to better match scarce nursing resources to projected demand. Nursing staff could be called in up to three days in advance if demand is expected to exceed nursing capacity. Conversely, nurses may be pulled from the schedule when demand is expected to be low. Flexible nursing schedules based on forecasts are feasible with enough advance notice (i.e., at least 24 hours). Optimizing the use of key nursing resources is a critical goal of the proposed work. In addition, FIG. 2 illustrates the type of information PICU-Forecast provides to aid in decision making regarding patient flow between the PICU and other components of the system. Ideally, PICU-Forecast would allow clinician managers to optimize PICU resources as an integral component of the children's hospital system. This would be done through informed management decisions based on forecasts which could also lead to proactive interventions to avoid bottlenecks in patient flow and underutilization (i.e., idle nursing resources).

The method also projects expected demand for nursing and bed resources up to 72 hours into the future. PICU-Forecast uses patient information that is available electronically in real-time to continually update and forecast as time progresses. PICU-Forecast includes sub-models describing the PICU current state, expected inflow (i.e., arrivals), and expected outflow (i.e., departures).

The method can be web-based or loaded onto a computer or tablet directly. Alternately, the method can be delivered in any other way known to one of skill in the art. The growing field of medical informatics has made extensive efforts to digitize patient and process related hospital information. This robust database of information can also be used to execute the method.

Flow equations are used to mathematically describe the relationship between each component model and how they will work in concert to forecast nursing care and bed demand. While this method will be described with respect to an exemplary PICU, this is not meant to be considered limiting, and the method can be used with respect to any suitable hospital unit. For example, in a PICU that consists of 26 beds consistently staffed by 16 nurses, patients demand either a 1:1 or 1:2 nurse-to-patient ratio. Thus, each nurse may be characterized as having a capacity of two nursing care slots, with 1:1 patients consuming both slots and 1:2 patients consuming one lot. With 16 nurses present in the PICU, there is a 32 (16×2) nursing care slot capacity. Whenever more than six patients require 1:1 nursing care, which is common, bed capacity is underutilized (i.e., constrained by nursing resources).

The flow equations are defined on a timescale where $t_0$ denotes the present time with any future time t up to 72 hours. Within this framework, $R_t$ is characterized as the number of nursing slots occupied at time t. $k_{jt}$ equals the number of nursing care slots occupied by the $j^{th}$ patient present in the PICU at time t. n represents the total number j patients in the PICU.
Therefore:

$$R_t = \Sigma_{j=0}^{n} k_{jt} \quad (1)$$

The true value of future nursing demand $R_t$ in reference to the present time t0 may be described as:

$$R_t = R_{t_0} + \Sigma_{i=0}^{a} Y_i k_{it} - \Sigma_{j=0}^{n} D_j k_{jt} \quad (2)$$

Where:
a=number of arrivals i between $t_0$ and t
Y=indicator variable for the $i^{th}$ arrival where 1=accepted and 0=rejected admission
k=nursing time slots occupied by each current patient j or future arrival i
n=number of patients j present in the PICU between $t_0$ and t
D=indicator variable for the $j^{th}$ patient where I=discharged and 0=present
*set all k=1 to calculate patient census at time t
Therefore a forecast $E(R_t)$ is characterized as:

$$\Sigma R_t = R_{t_0} + E(\Sigma_{i=0}^{a} P_i k_{it}) - E(\Sigma_{j=0}^{n} q_j k_{jt}) \quad (3)$$

Where:
$p_i$=probability of $i^{th}$ arrival being accepted for admission between $t_0$ and t $q_j$=probability off $j^{th}$ patient discharge or death between $t_0$ and t
*set all k=1 to calculate expected patient census at time t
Flow equation (3) also allows nursing demand $E(R_t)$ to be forecasted at any future time t up to 72 hours.

However, practical application of the model will involve producing forecasts updated every 3 hours in 3 hour intervals up to 72 hours into the future. Thus, 24 (72/3) discrete point forecasts of $E(R_t)$ with coinciding confidence intervals will be updated as the model runs in time. The nursing care slot variable k may be set to 1 for all patients to render forecasts of patient census (i.e., bed demand) instead of nursing demand.

Figure 3:
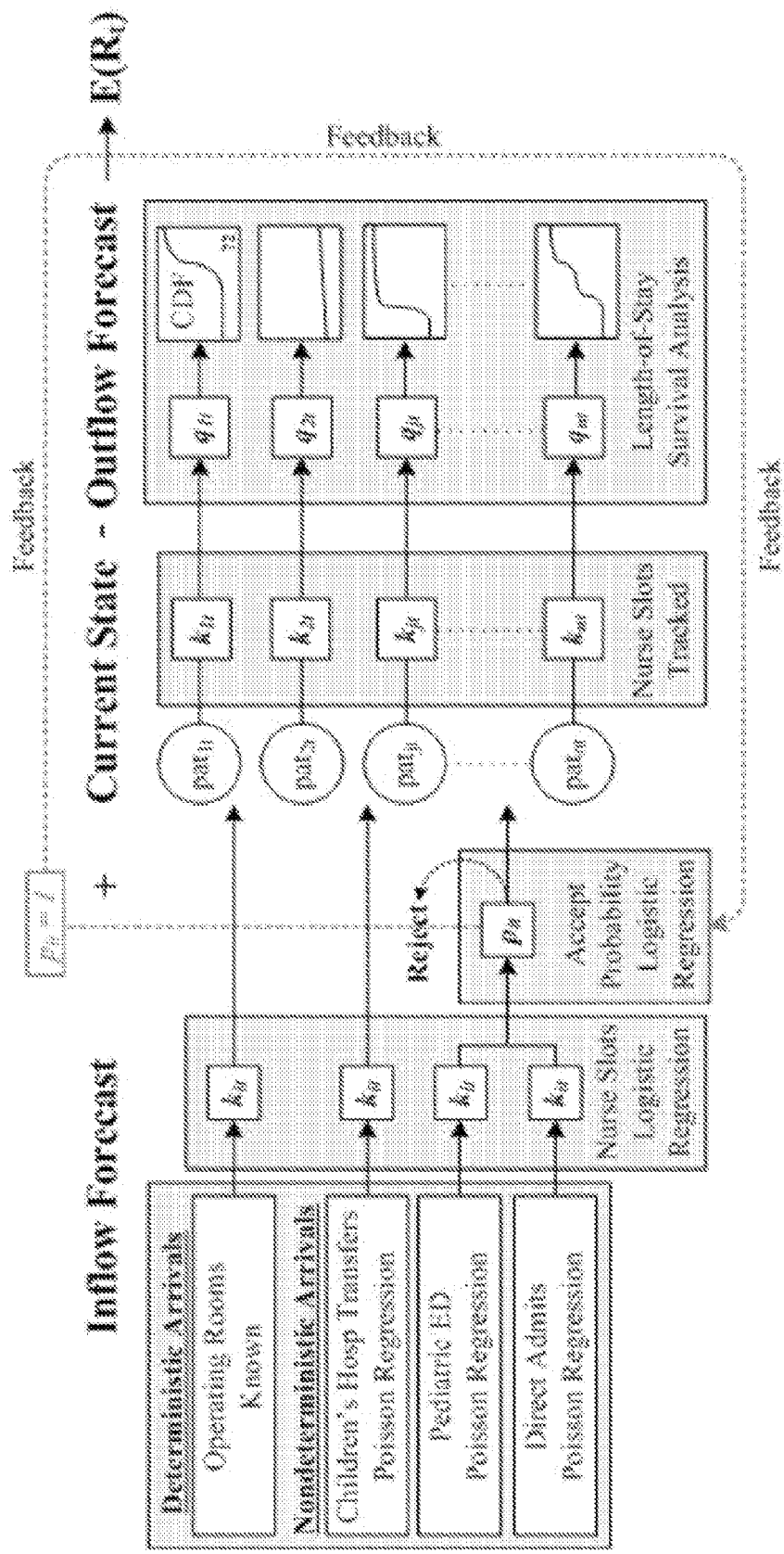
FIG. 3 illustrates a diagram outlining inflow and outflow models and their integration according to an embodiment of the invention.

FIG. 3 illustrates a diagram outlining inflow and outflow models and their integration. Accurate inflow and outflow forecasts will result in accurate forecasts of demand. The global model will produce both unadjusted and adjusted forecasts of nursing demand $E(R_t)$ as demonstrated by the feedback mechanism. Unadjusted forecasts are made assuming that the probability of admission acceptance is 100% (set $p_{it}=1$) for all i arrivals between $t_0$ and t. Increases in unadjusted forecasts of demand are inversely proportional to the probability of admission. Including the calculation of probability of admission acceptance within the model produces adjusted estimates of forecasted demand, along with the expected number of rejected patients over a given time interval. Thus, unadjusted forecasts provide feedback which dampens true (i.e., adjusted) forecasts of the system. The inflow model, outflow model, feedback mechanism and predictors variables will be described in further detail.

Forecasting PICU inflow includes predicting the number of arrivals a between time $t_0$ and t along with their corresponding probability of admission $p_i$ and expected nursing care slots needed $k_i$. Each of these expected values is predicted jointly to generate forecasts of inflow demand. A description of how each of these values are predicted and integrated follows.

Figure 4A:
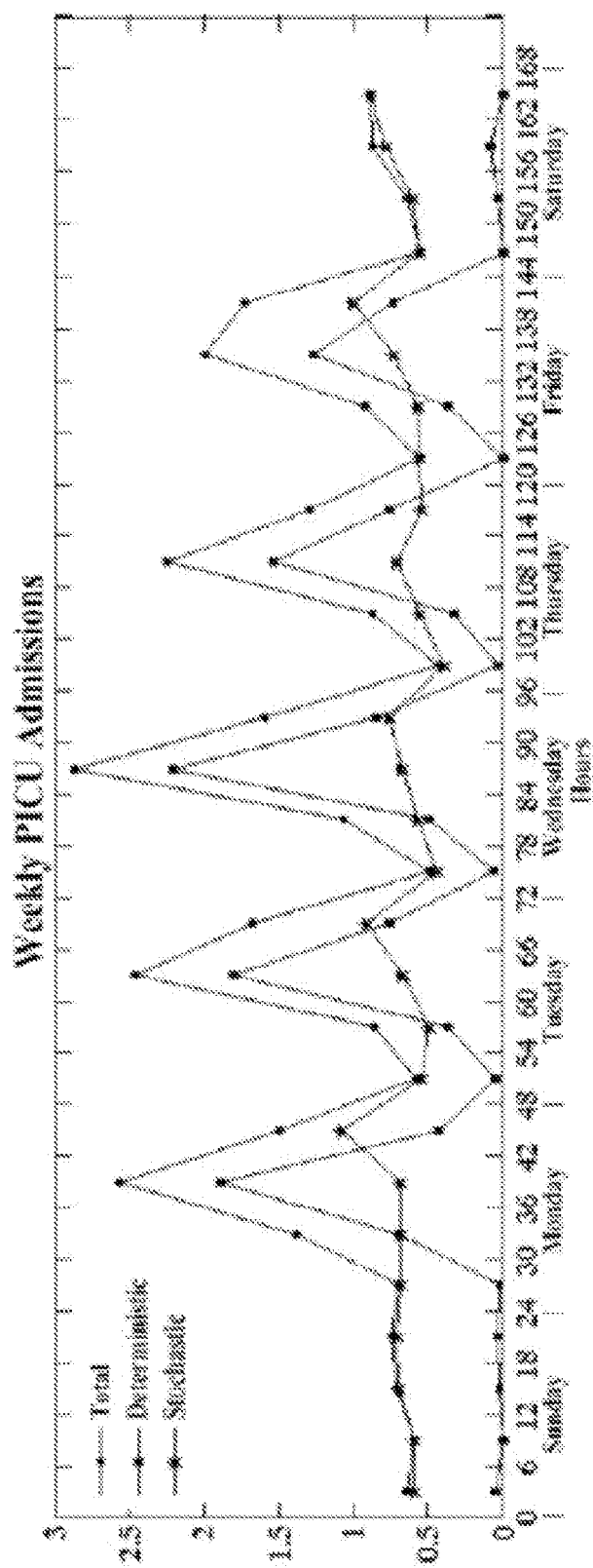
FIG. 4A illustrates a graphical view of the ensemble average of counts for total, deterministic, and stochastic arrivals in 6 hour intervals over the course of a week according to an embodiment of the invention.
Figure 4B:
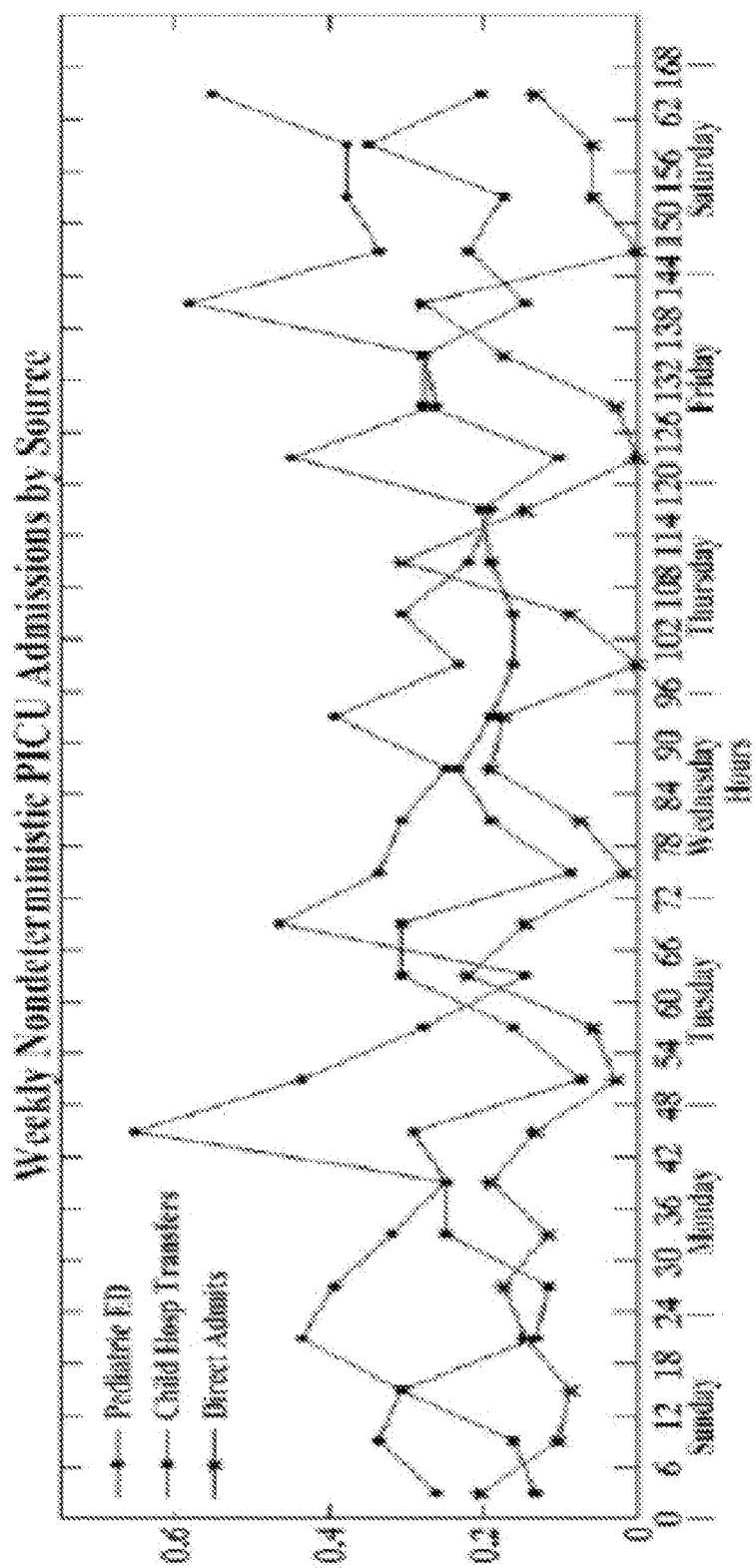
FIG. 4B illustrates stochastic arrivals decomposed by admissions source according to an embodiment of the invention.

As outlined, arrivals are categorized as stochastic (i.e., unscheduled) or deterministic (i.e., scheduled). The expectation of stochastic arrivals are forecasted and combined with known deterministic arrivals to comprise all arrivals a between time $t_0$ and t. It is important to note that all arrivals including rejected patients will be predicted. This includes direct admission requests rejected and pediatric ED patients transferred to other facilities because of lack of available capacity. FIG. 4A illustrates the ensemble average of counts for total, deterministic, and stochastic arrivals in 6 hour intervals over the course of a week. A strong temporal pattern in deterministic arrivals contrasts the more homogenous pattern displayed by stochastic arrivals. However, when the stochastic arrivals are decomposed by admission source, as illustrated in FIG. 4B. Each admission source demonstrates a heterogeneous and distinct pattern over time. Furthermore, it is hypothesized that different hospital and environmental factors influence the conditional arrival count distribution from each source over time. As a result, arrivals from each stochastic source will be predicted separately.

Different factors are expected to influence the conditional arrival count distribution of each admission source over time. Factors that affect arrival counts from the pediatric ED include: ED wait room count, number of high-acuity (i.e., severely ill or injured) patients being treated in the ED, season, temperature, precipitation, holidays, ED diversion status and temporal factors (i.e., time-of day, day-of-week). Factors that affect arrival counts from children's hospital transfers include: number of patients at several inpatient locations, surgical caseload, hospital diversion status and temporal factors. Factors hypothesized to effect arrival counts from direct admissions include; season, temperature, precipitation, holidays and temporal factors.

Figure 5:
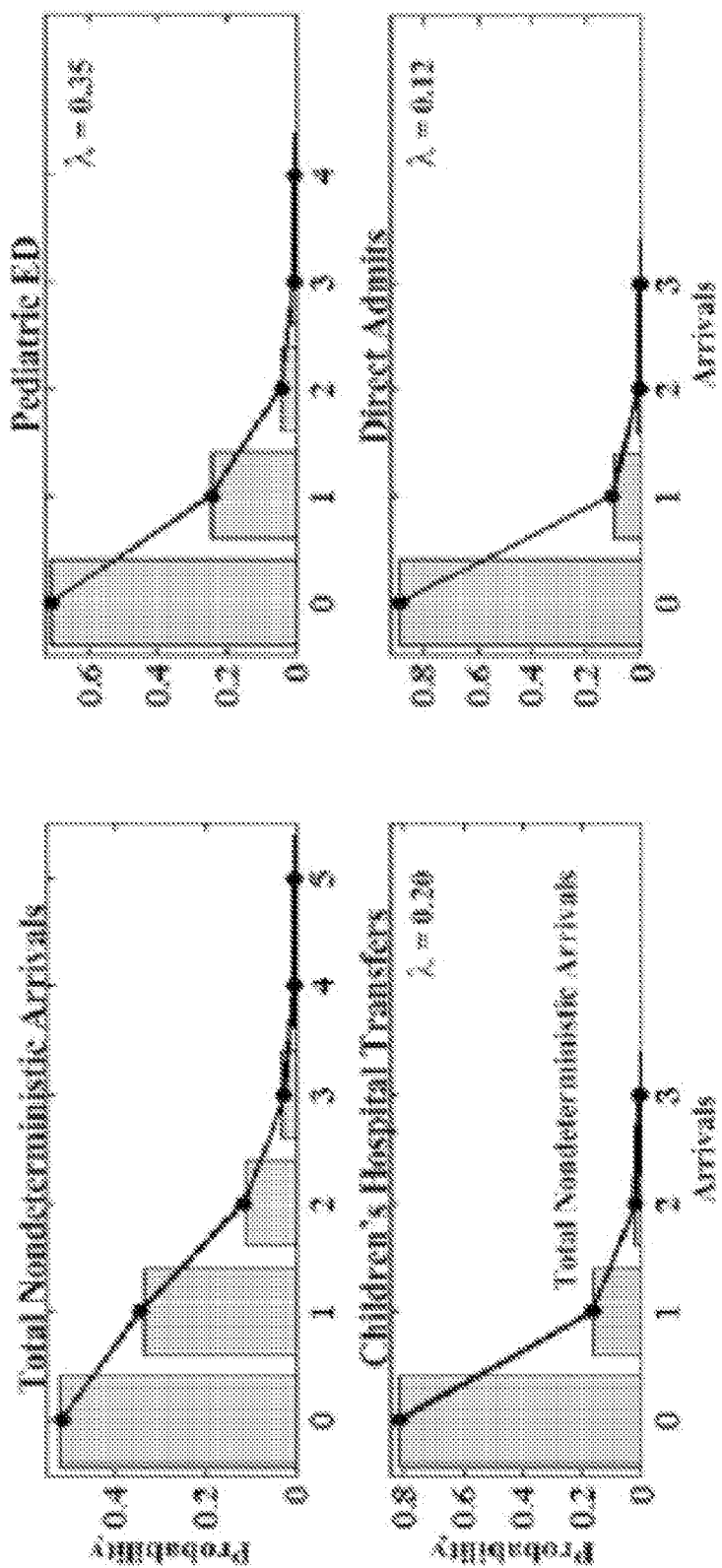
FIG. 5 illustrates a graphical view, of the overall and source specific arrival distribution according to an embodiment of the invention.

Poisson regression is used to model the relationship between arrival counts and predictor variables from each stochastic source. Arrival counts following a Poisson distribution is a common characteristic of counting processes with independent observations. The assumption of independence is conceivable because in the absence of a catastrophic event or infectious outbreak, individuals experience injuries or become ill independent of one another. This assumption is scrutinized by characterizing the autocorrelation within each stochastic admission source. Autocorrelation was measured for counts over intervals from 1 to 72 hours, lagging up to 3 weeks. Non-significant autocorrelation estimates (i.e., less than may be observed by chance in random counting process) were found over all interval lengths. However, because a latent process can introduce autocorrelation into parameter driven models, such as Poisson regression, this will be accounted for this potential bias by applying an iterative weighted and filtered least-squares algorithm developed by the investigators. PICU arrivals that are independent and fluctuate over time as a function of known factors are well-approximated by a Poisson distribution. FIG. 5 illustrates a graphical view of the overall and source specific arrival distribution. As illustrated in FIG. 5, these are equidispersed and closely match a Poisson distribution for a 6 hour interval. Similar close fits are evident for all intervals.

Arrival count distributions exhibit heterogeneity over time as illustrated in FIG. 4B. Temporal factors (i.e., month, day-of-week, and time of day) can be predictive of stochastic arrivals. The arrival data for temporal patterns will be examined to determine whether there are possible interaction effects between temporal factors or between temporal factors and other patient or hospital characteristics. Depending on the arrival rate, the temporal pattern can be smoothed over discrete time intervals by fitting sine and cosine curves. If the arrival counts vary substantially over time, the arrival rate function can be approximated as a piecewise constant. A test of the null hypothesis that arrivals form a non-homogeneous Poisson process can be used, as well as a methodology to assess arrival rate stationarity in order to set cut points (i.e., time intervals). Methods of using temporal factors as predictor variables and stratifying models based upon stationary time intervals will be explored to determine which methodology yields the most accurate predictions.

The Poisson regression models developed for each admission source are compared to common observation-based arrival forecast methodologies. Autoregressive integrated moving average (ARIMA) and autoregressive moving average model with exogenous inputs (ARMAX) will be explored. These models are expected to be less accurate as a result of low autocorrelation exhibited in the data and low counts for smaller time intervals. However, these models will be applied and compared to provide reference.

In addition to predicting the conditional arrival count distribution, a corresponding probability of admission $p_i$ is calculated for each arrival from the pediatric ED and direct admissions. The PICU-Forecast system will predict the number of patients expected to be rejected over time interval $t_0$ to $t$, which is an important performance measure of the PICU system.

A logistic regression model will be used to determine the relationship between predictor variables xi and probability of admission. Predictor variables will include admission source and unadjusted forecasts of demand (i.e., $p_i$=1) as described above. Thus, unadjusted forecasts of demand that have potential to exceed nursing or bed capacity will decrease the likelihood of future stochastic arrivals i being admitted. Conversely, forecasted demand that is unlikely to exceed capacity increases the probability of admission. This feedback mechanism is only applied to stochastic arrivals from direct admissions and the ED because only these patients are permitted to be rejected (see FIG. 4). Probability of admission $p_i$ for the $i^{th}$ arrival is derived as a function of $x_i$ using known binomially distributed data (indicator variable: admit=1, reject=0) for $a_i$ Bernoulli trials (i.e., arrivals) where $$P_i = E(Y_t \mid X_i) = \frac{1}{1 + e^{-\left(B_0 + B_1 x_{1,i} + B_k x_{k,i}\right)}} \quad (4)$$

Thus unadjusted (all $p_i$=1) forecasts of nursing demand and admission source information provide feedback ($x_i$) to this regression model allowing $p_i$ for each $i^{th}$ arrival to be calculated. This novel feedback mechanism controls for dependence between inflow and outflow which is further described below.

The final component of the inflow model requires predicting demand for nursing care slots $k_i$ (1 or 2) for all new arrivals i using logistic regression. The probability of an arrival consuming 2 nursing time slots ($k_i$=2) will be calculated again for binomially distributed data Si (2 slots=1, 1 slot=0) as a function of predictor variables $x_i$ where $$K_i = E(S_i \mid X_i) + 1 = \frac{1}{1 + e^{-\left(B_0 + B_1 x_{1,i} + B_k x_{k,i}\right)}} + 1 \quad (5)$$

A one is added to adjust, such that a forecasted arrival with an 80% chance of consuming 2 nursing time slots will have a $k_i$ value equal to 1.8. Predictor variables $x_i$ for stochastic arrivals will include admission source and temporal factors. This is the only information known at time $t_0$ about forecasted arrivals i. For deterministic (i.e., surgical) arrivals, predictor variables will include information categorizing type of surgery and patient demographics. Nurse care slot predictions for deterministic arrivals are expected to be more accurate as a result of availability of highly descriptive clinical and demographical information at $t_0$.

To forecast PICU outflow, patient length-of-stay is predicted in the form of a cumulative density function (CDF) such that the probability of discharge $q_{j,t}$ may be calculated. For each patient j the corresponding nursing care slot value k must also be tracked over time, because it is subject to change. Thus, the expected value for probability of discharge $q_{j,t}$ must be linked to correct values of $k_j$ to generate forecasts of outflow demand. A description of how these values are predicted and integrated follows.

Patient length-of-stay includes two phases. The first phase encompasses the time from patient arrival to decision to discharge. The second phase includes the time from discharge decision until the patient physically exits the PICU. Both phases of length-of-stay can be expressed in terms of a CDF such that the probability of discharge $q_{j,t}$ may be calculated over each 3 hour interval from 3 to 72 hours into the future. Similar calculations may be derived from the probability density function (PDF) or survivor function (SF). However, the CDF will be consistently referred to in describing a patient's probabilistic distribution of length-of-stay.

Figure 6:
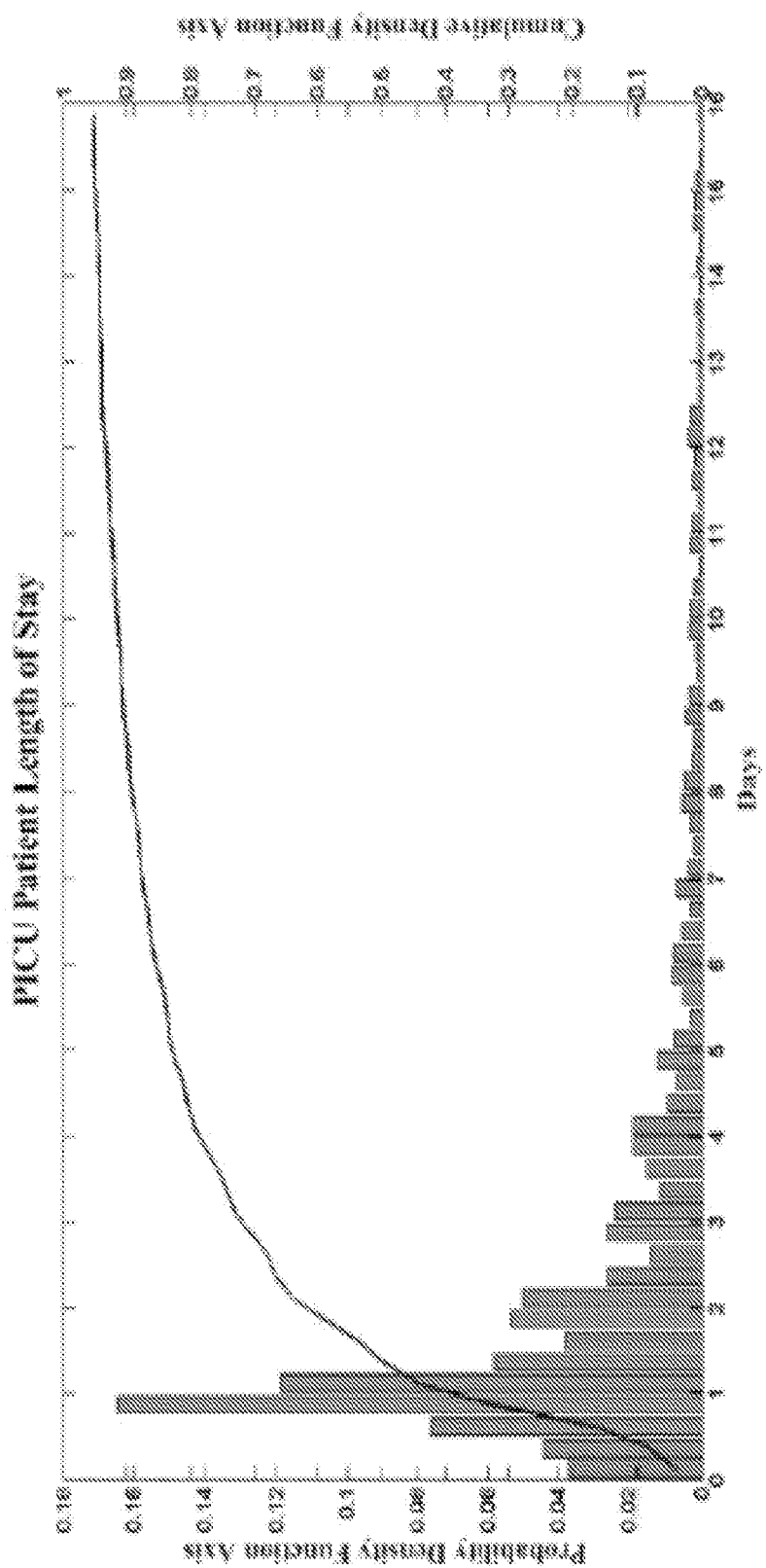
FIG. 6 illustrates the total length-of-stay (LOS) for patients according to different graphical models according to an embodiment of the invention.

FIG. 6 illustrates the total length-of-stay for all PICU patients in the form of a CDF and PDF. The right-skewed PDF is common of hospital length-of-stay data. PICU length-of-stay ranged from a minimum of 90 minutes to a maximum of 127 days; however 97% of patients had a length-of-stay of less than 16 days. Approximately 71% of patients exit the PICU within 72 hours of arrival. The remaining 29% of long-stay patients consume 78% of total bed-hours.

For both phases of patient length-of-stay, survival analysis regression methods are used to predict future length-of-stay in the form of a CDF. As time progresses, the patient has a probability of disposition over defined time intervals conditioned on the patient's current length of stay c. the CDF is denoted, $F(x_0)$ and PDF, $f(x_0)$ as functions of predictor variables $x_0$ at present time $t_0$ then the probability of patient receiving a disposition $q_{jt}$, between $t_0$ to t is calculated as $$q_{jt} = \frac{\int_c^{c+t} f(x_0)dx}{1 - F(c)} \quad (5)$$

Factors that influence patient length-of-stay, such as patients' clinical condition and hospital environment change over time. Thus, it is important that the outflow model update itself with current covariate information regularly (i.e., every 3 hours) throughout each patient's PICU stay. In the outflow model, updated information $x_0$ conditioned for current length-of-stay c is used to predict probability of disposition $q_{jt}$ into the future. Application of the survival analysis regression model involves creating updates of each patient's future CDF every 3 hours based on current predictor information conditioned on current length of stay.

To accomplish this, survival analysis regression methods used to quantify factors that affect length-of-stay on a cohort of patients in "study time" must be applied in "calendar time" (i.e., real-time). Study time refers to the artificial alignment of all patient arrivals in time such that survival analysis models may be applied. Alignment allows survival analysis regression methods to determine the probability of an event, conditioned on remaining at risk (and therefore time elapse) as a function of covariates. But the prediction models for the expected number of children in the PICU in each future 3 hour interval requires application of the survival model predictions in calendar, not study time. The expected numbers are sums over all children of their probability of remaining in that interval that can be directly calculated from their survival function, estimated in study time.

Three variations of survival analysis will be used to predict each phase of length-of stay: (1) Discrete-time logistic regression; (2) semi-parametric proportional hazard regression, and; (3) parametric regression. The main advantage of discrete-time logistic regression is that it is likely to produce the most unbiased, stable estimates of the three methods because no baseline survivorship function is estimated. In this approach, logistic regression models of expected probability of event (e.g., discharge) are computed for time intervals $t_0$ to t where, t=[3, 6, 9 . . . 72] hours in the future. Event probabilities may be connected through simple linear spline interpolation to create a future CDF. An additional advantage of this model is that temporal factors may be accounted for within discrete time intervals without compromising stability. Semiparametric and parametric survival regression models could also be used as could any other computationally efficient mathematical model to predict length-of-stay.

To employ semi-parametric or parametric survival regression models, each patient arriving to the PICU must be assigned a specific patient cluster based on predictor information collected at arrival. A cluster assignment must be made to associate a baseline survivor function (i.e., initial CDF). Semiparametric proportional hazard regression models are advantageous in that there are no assumptions concerning the nature or shape of the underlying survival distribution. The Nelson-Aalen estimate is used to empirically estimate the baseline survivor function at arrival based on arrival cluster assignment.

Parametric regression models can also be used. Parametric regression models simultaneously describe the underlying distribution of survival function and characterize how the distribution changes as a function of predictor variables. Parametric models are more apt to predicting survival time; however the survivorship function must fit to standardized probability distributions. This assumption may not be met when applied to hospital length-of-stay, where temporal factors (e.g., physician rounds) cause discharge events to happen at specific times-of-day. This creates daily patterns in the underlying PDF of length-of-stay, as illustrated in FIG. 6. The fundamental trade-off in using semi-parametric versus parametric models is that semiparametric models provide less bias in their estimates; however this can lead to instability (i.e., high variance). Parametric models are more biased in estimation, but will be consistent in generating more stable (i.e., lower variance) estimates over time.

For phase one of length-of-stay, arrival time to discharge decision time, clinical and treatment factors will be most important, as shown in Table 1. A goal in selecting predictors will be to only include variables that improve predictive power significantly. Thus, reducing the complexity and size of the state space the model will operate within. Forecasting this phase of length-of-stay involves using provider orders as predictor variables. Trend (i.e., slope) information will be incorporated as predictor variables. Medications administered in the PICU are broken into five categories; (1) emergent, (2) PICU administration only, (3) urgent, (4) maintenance/stabilizing, and (5) chronic. The types of medications, dosage and rate of change are expected to be highly predictive of future length-of-stay. Also several medication pairs will be examined through interaction effects because pairing is considered indicative of higher severity of illness and longer lengths-of-stay.

Predicting time from decision to discharge until patient is transferred out of the PICU will be accomplished using the same survival analysis regression methods discussed above. However, the variables used to predict this phase of length-of-stay are operational and temporal. Patients transferred to other children's inpatient units (84%) will have their future unit specified (i.e., available in transfer order) which is a function of age and illness, as illustrated in FIG. 1. The occupancy in that unit over time is hypothesized to predict future time-to transfer and will be included as a predictor variable. Temporal variables (i.e., time-of-day, day-of-week) will also be included as predictor variables to account for patterns in admissions and discharges in future inpatient units. This component of the model produces a useful bi-product to help quantify blocking in patient outflow. A forecast for patients discharged home is also being employed as a function of temporal variables only.

TABLE 1

Length-of-stay predictor variables

Medication Orders

Emergent medications group; PICU administration only medication group; Urgent medication group; Maintenance medication group; Chronic medication group; Medication dose trends; Medication pairs

TABLE 1-continued

Length-of-stay predictor variables

Breathing Support Orders

Mechanical ventilation status (on, off); Mechanical ventilation mode (APRV, HFOV, PCV); Mechanical ventilation rate; Mechanical ventilation rate trend; Mechanical ventilation pressure; Mechanical ventilation pressure trend; Oxygen delivery; Re-intubation; Face mask (on, off); Nasal cannula (on, off); Nasal cannula liter flow; Nasal cannula liter flow trend Feed Orders Nothing per orem (nothing by mouth); Nasogastric feeding tube; Gastric feeding tube; Liquid diet; Solid diet Physiological Measures PH; PaO2; PaCO2; Systolic blood pressure; Glucose; Heart rate; Temperature; Potassium; Creatanine; White blood cell count; Platelet count; Aspartate transaminase; Prothrombin time Administrative (procedural, demographic)

Admission source (ED, OR, Inpatient Floor, Direct Admit); PICU admission diagnosis; Surgery type (OR patients); Acuity level (ED patients); Age; Gender; Race PICU admission diagnosis Temporal Current patient length-of-stay; Month; Time-of-day; Day-of-week It is important to note that $q_{jt}$ may denote death. However, only 2.8% of patients die in the PICU. These patients experience degradation in their clinical condition compared to improvements experienced by patients discharged. Inverse trends in the clinical condition of these two groups of patients are expected to confound the analysis. Thus, patients who die in the PICU will be subject to separate analysis using the same methods, or a competing hazard for this small group of patients will be introduced.

Every 12 hours at the change of nursing shift, the nursing care demand for each patient currently in the PICU is assessed. Nursing care slot needs $k_j$ are collected for each current PICU patient j; however these needs are subject to change before the next collection interval. Specific medication orders, breathing support orders and feed orders, shown in Table 1, trigger changes in this value. These triggers have been described by PICU clinicians, but will be validated using the nursing assignment data available every 12 hours (i.e., 7 am and 7 pm). Trigger events will update $k_j$ at each 3 hour interval. It was determined that forecasting $k_j$ within a 12 hour interval (i.e., before the value was known) would provide low marginal value to the accuracy of the model.

Each sub-model, as illustrated in FIGS. 4A and 4B, include the overall PICU-Forecast model will be evaluated individually for accuracy. Arrival, length-of-stay, nursing care slot and admission likelihood models all forecast conditional probabilistic distributions at future times t. Forecasted distributions are compiled using Equations 1-5 to produce point estimates of expected nursing and bed demand. Corresponding confidence intervals associated with these distributions will be compiled likewise to produce confidence interval point estimates. The accuracy of point estimates with confidence intervals will be evaluated for each of the sub models as well as the overall PICU-Forecast model.

Standard measures such as Theil's U, mean absolute percentage error (MAPE), mean absolute deviation (MAD) and others will be used to assess accuracy of PICU-Forecast at each future time point. In addition, measures which specify the percent within a pre-determined error window will also be calculated. The error window will be defined by clinician managers (i.e., users) as to what level of accuracy will allow them to comfortably make decisions based on forecasts. Quantitative comparisons between using more predictive information (i.e., computationally more complex) and accuracy will continually be assessed, with the goal of creating the most simple model that may be transferable to other hospitals.

Lastly, it must be anticipated that the implementation of the forecasting model improves the behavior concerning management of the PICU. As behavior changes, the forecasting model must be tractable. All regression model coefficients used in the analysis are updated weekly weighting recent information more that distal information. Time-weighted regression estimates will allow the model to adapt to behavioral change and remain accurate as the model moves over time.

For example, when length-of-stay decreases, beds are vacated quickly leading to unoccupied space that can accommodate an increase in admissions. Conversely, increased length-of-stay leads to congestion and blocking which decreases admissions rate. Not accounting for inflow and outflow dependence can lead to misleading models and inaccurate forecasts. The novel feedback mechanism accounts for this dependence by altering admission probability based upon projections of resource availability.

Another potential methodological contribution involves the transformation of the temporal component of survival analysis from "study time" to "calendar time" as discussed above. This involves applying survival analysis methods used in study time and applying them in calendar (i.e., real-time). In addition, methods to incorporate rich physician order information, especially trend data into survival analysis regression can be used. The new and adaptive methods developed in the proposed work are likely to be applicable to modeling flow systems (i.e., queuing science, discrete event simulation, forecast modeling) in other domains besides health care.

Broader impacts of the proposed work include the development of a tool aimed at optimizing pediatric critical care resources to improve access for critically ill and injured children. Pediatric and adult critical care units care for acute patients at highest risk of death or morbidity who have proven to greatly benefit from these specialized services. Optimizing these resources as an integral component of the hospital system is likely to improve operations of an entire hospital and possibly improve public health within a region.

The project addresses the need to improve management of nursing resources. More flexible nurse scheduling based upon accurate real-time projections may be an effective method to mitigate the effects of the large-scale nursing shortage. Forecasting days in advance to provide ample time to acquire or relieve nurses for their full 12 hour shift may be a feasible method of both improving access and decreasing costs.

As noted above, the method can be generalized to any hospital or hospital unit with capable information technology known to one of skill in the art. Reducing the complex state space to only include only the most pertinent variables is necessary in potentially applying these models to other facilities. Application to other health care facilities will be emphasized throughout the model development phase.

An exemplary study of 2,178 consecutive pediatric intensive care unit (PICU) patients over a 16-month time period was conducted to determine and develop the described method. 70 (3.2%) patients that died in-hospital and 46 (2.1%) patients with missing or incoherent data were excluded. Thus, the final cohort consisted of 2,062 patients with an average age of 6.75 years ranging from less than 1 (23%) to 21 years. All patients were cared for in a 26-bed PICU, which is part of a 180-bed children's hospital located within an urban, academic medical center. Patients' source of admission were the OR (39%), pediatric ED (26%), intrahospital transfers (18%), and referrals from external healthcare facilities (17%). PICU providers use a CPOE system to directly enter all orders including: diets, activity, medication, laboratory tests, radiology tests, and procedures.

PICU LOS, source of admission, readmission status, age and all time-stamped provider orders 6-hours prior to PICU arrival until PICU discharge were collected. An expert panel of three pediatric physicians and one nurse selected key orders hypothesized predictive of LOS. Selected orders fell into the following categories: activity, consults, diet, extracorporeal membrane oxygenation (ECMO), foreign body, laboratory, mechanical ventilation, enteral medications, infused medications (vasoactive, opiate, other), injected medications (electrolytes, sedatives, muscle relaxants, other), and transfusion. Each of the categories was comprised of order groups. In total, 770 unique orders fell into 60 groups recognized by the forecast model. For example, there were 30 unique dietary orders grouped as either: withhold food (NPO), clear liquid diet, full liquid diet, formula/human milk, or regular diet. Additional information such as ventilation frequency (i.e., continuous versus nightly) or laboratory order frequency was also used to stratify order groups. Preliminary discrete-time logistic regression models were displayed to the expert panel in an iterative process to further refine order selection and grouping. Order groups recognized by the model will hereafter be referred to as orders.

Patients' future LOS was predicted using survival analysis. Discrete-time logistic regression models were developed to predict the probability of a patient being discharged within each 6-hour interval up to 72 future hours. Twelve separate models (i.e., 72 divided by 6 hours) were used to predict likelihood of discharge across each interval. The models estimate the probability of discharge in a specific interval given the patient will be present the interval prior. The set of model estimates are joined by the following function where: (a) represents an individual model's probability estimate, and (p) represents the joint probability estimate for the (ith) future time interval:

$$P_i = P_{i-1} * \frac{1 - a_{i-1}}{a_{t-1}} * a_i \quad (6)$$

This function produces a coherent probability density function profiling a patient's probability of discharge with emphasis on predictions closest to the current time (i.e., i0) being most accurate.

The joint model is conditioned on fixed information such as a patient's age, source of admission, and readmission status, but is updated in near real-time based on dynamic information such as patient's current LOS, temporal factors, and provider orders. Fixed and dynamic information serve as model predictor variables each time a forecast is made. Patients' current LOS is grouped as either being short stay (<3 days) or long stay at the instant the forecast is made. Temporal information includes the day-of-week, and time-of-day (i.e., grouped by midnight to 6 am, 6 am to noon, noon to 6 pm, and 6 pm to midnight) the forecast is made. Dynamic order information is extracted from CPOE in the interval 6 hours prior to forecast time. For each patient's 6-hour order extract, all 60 orders are indicated as either present or not. For example, if a lactic acid laboratory order was placed for a patient within the past 6 hours, this variable was listed as present. Medications were grouped by type and administration method. In addition, counts of medications by administration method (i.e., enteral, infusion, injection) were examined as predictor variables.

Figure 7:
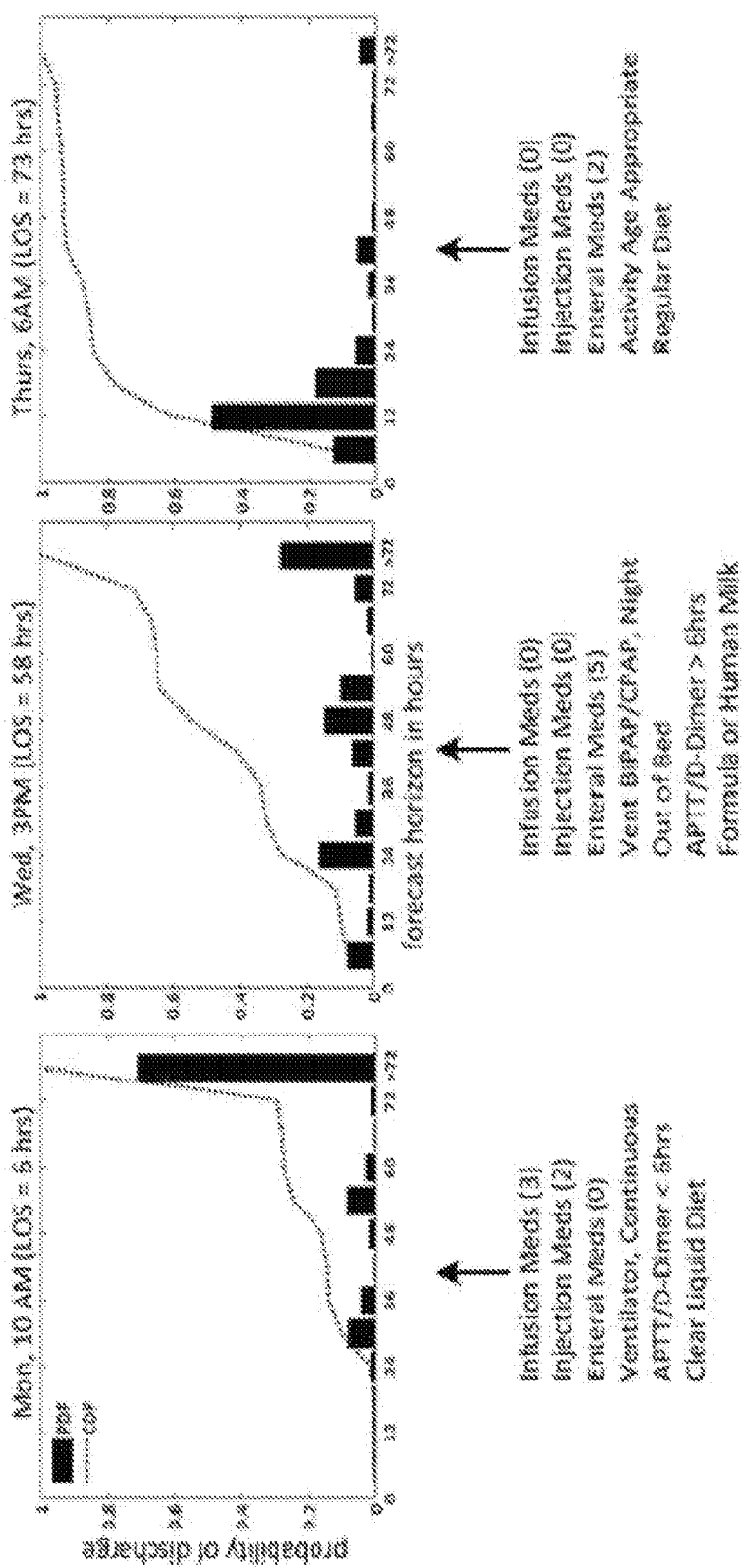
FIG. 7 illustrates a graphical view of a forecast during a patient LOS according to an embodiment of the invention.

An example forecast, at three time points (i.e., sliding window forecasts) during a patient's LOS may be seen in FIG. 7. Output forecasts are updated over time to reflect changes in a patient's conditions based on orders. The example forecasts are for an 8 year old patient admitted through the ED, with the leftmost plot representing the patient 6 hours into their PICU stay. Within the previous hours the patient had present orders for: 3 infused medications, 2 injected medications, continuous ventilation, either activated partial thromboplastin time (APTT) or D-Dimer laboratories with a frequency of less than 6 hours, and clear liquid diet (see order set below plot). At this point the patient is likely to be discharged after 3 days, as evident by the forecast density. The middle plot represents this same patient 58 hours into their stay with an order set reflecting a progression in health status, but still uncertainty about future LOS exists. The right plot is again the same patient with an order set indicating further progression and likely discharge within the next 18 hours. The temporal predictor variables (e.g., time-of-day) produce the harmonic peaks most evident in the middle plot. This is designed to account for PICU processes (e.g., rounds, staff shift changes, etc.) that make it most likely for all patients to be discharged during certain portions of the day.

Figure 8:
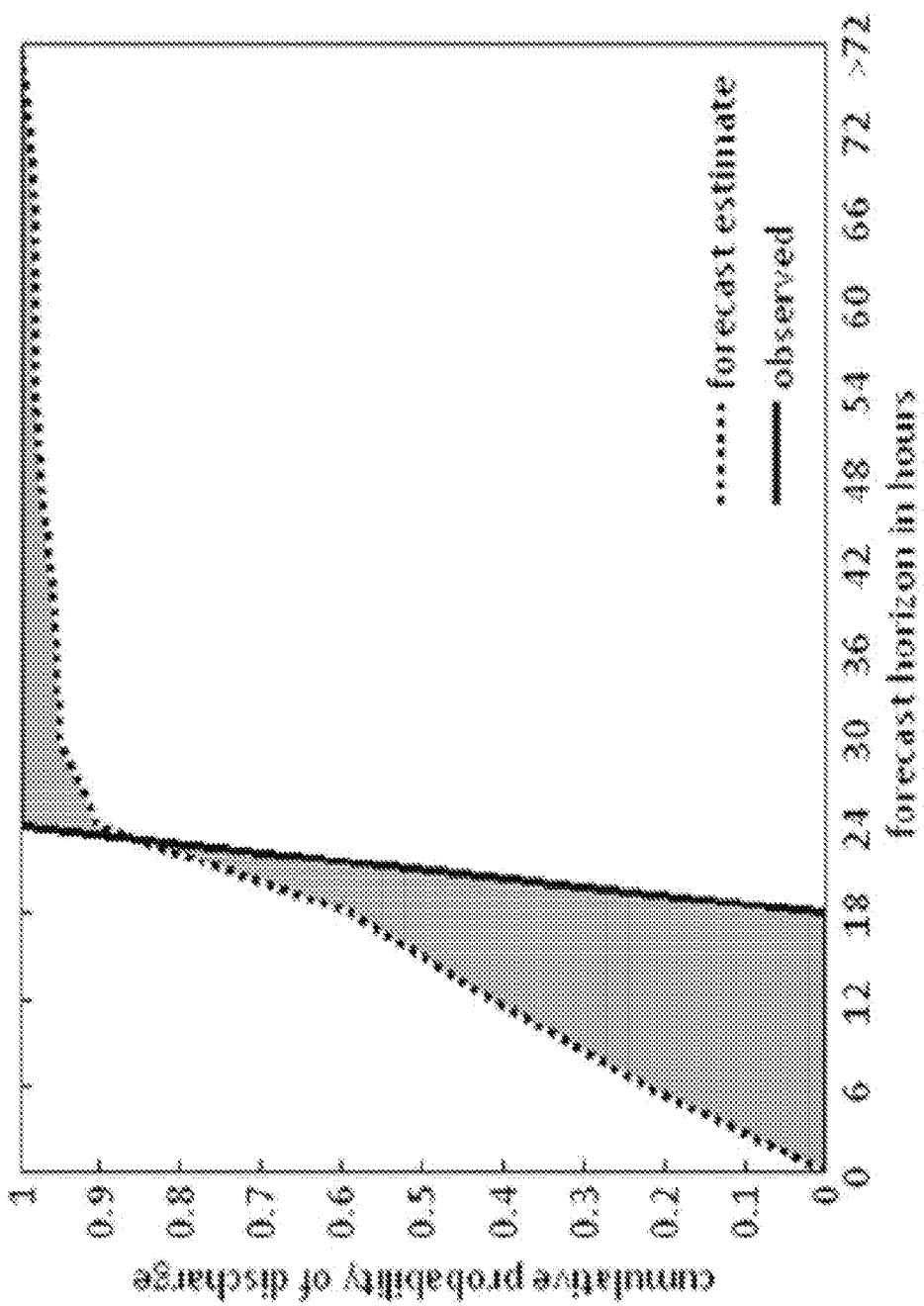
FIG. 8 illustrates a graphical view of how rank probability scoring (RPS) is measured for a patient discharged between 18 and 24 hours from forecasting according to an embodiment of the invention.

Sharpness and calibration are the most important characteristics for evaluating the accuracy of probabilistic forecasts. Sharpness assesses the variance (i.e., uncertainty) of probability estimates around the actual observation (i.e., discharge time). A forecast that places a high concentration around the time of actual observation is sharper and more certain than a density forecast estimate with higher spread. Rank probability scoring (RPS) was used to evaluate the sharpness and accuracy of each patient's sliding window forecasts and also formed the basis for selecting the most highly predictive orders. The RPS is a measure of the difference (i.e., integral) between the cumulative distribution of a forecast and actual observation and has been shown to minimize mean absolute error. An example of how the RPS is measured for a patient discharged between 18 to 24 hours from forecast time is illustrated in FIG. 8. This measure was calculated for each sliding window forecast (N=29,749) for all patients in the cohort. Forecasts were also evaluated graphically using calibration curves comparing forecasted mean probability of discharge to observed probability. The utility of orders in predicting LOS was further scrutinized by comparing the order-based forecast model RPS to forecasts created from the empirical LOS distribution and from a model solely relying on fixed and temporal dynamic variables (i.e., order-less model). Empirical sliding window forecasts were constructed by applying the future rescaled empirical distribution given patients' current LOS.

The order selection objective was to determine the most highly predictive set of orders from the 60 hypothesized to influence LOS. Univariate and forward stepwise analysis was used with the objective of minimizing mean RPS across all forecast windows. Fixed predictor variables were initialized in all analysis with univariate and stepwise procedures only conducted on orders. Marginal utility of each final model order was examined with the aim of minimizing orders included (i.e., complexity) while maximizing predictive accuracy.

Cross-validation was used to evaluate the regression model's out-of-sample predictive performance (i.e., mean RPS). Patients were split into 80% training and 20% testing sets. Model parameters were generated from the training set with RPS evaluated against the test set. This process was iterated 100 times to ensure stability of both predictive performance and parameter estimates.

Figure 9:
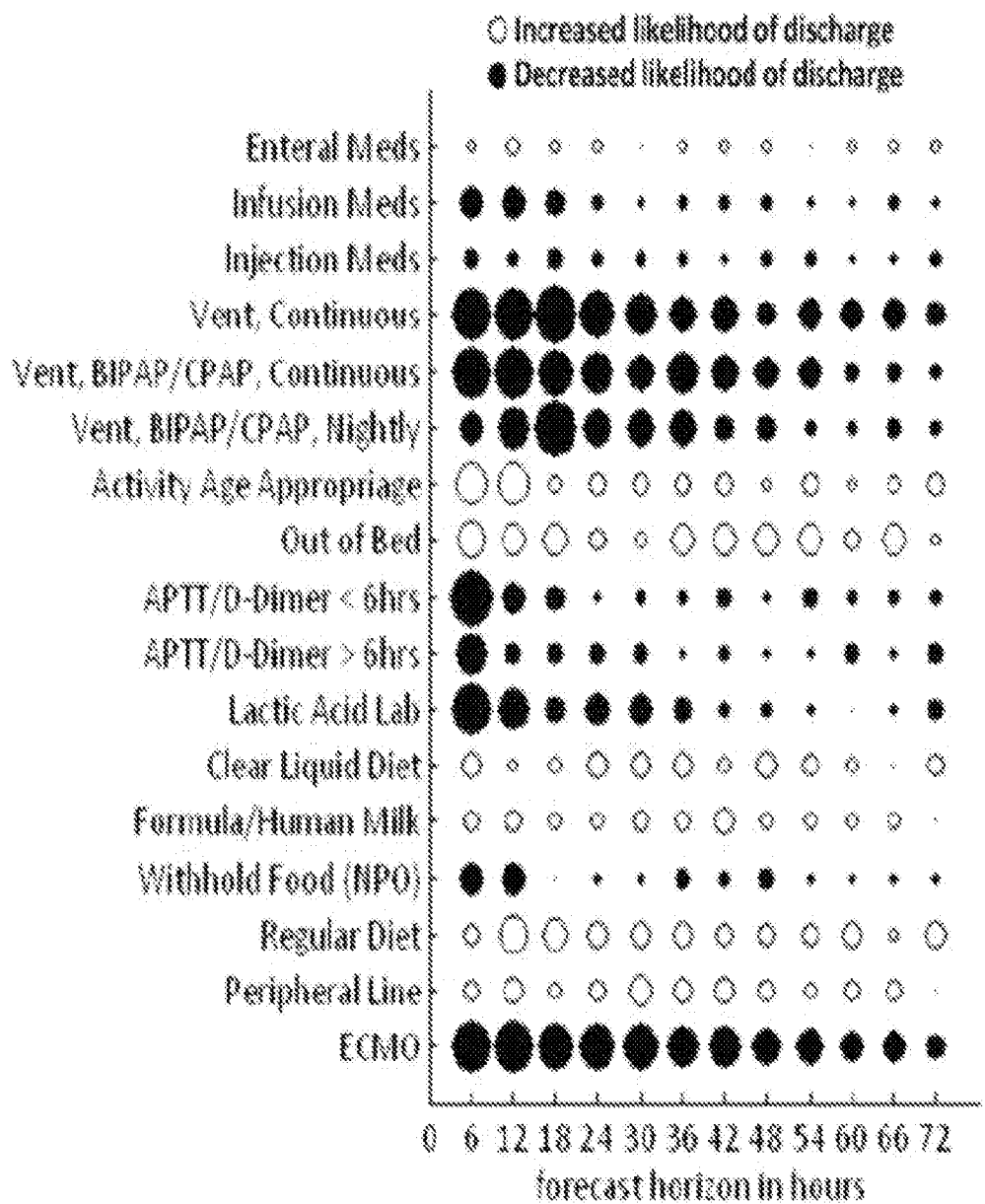
FIG. 9 illustrates a graphical view of predictive power with respect to forecast horizon according to an embodiment of the invention.

The distribution of PICU LOS was heavily right-skewed with a mean of 3.5 days (95% CI 0.3 to 19.1) and median of 1.7 days (IQR 22.2 to 3.8). The set of orders most predictive of LOS is seen Table 2. Odds ratios estimating patients' likelihood to remain in the PICU for the next 6 hours (i.e., first forecast interval) are displayed. Additional orders were predictive, but did not significantly improve model accuracy. All orders evaluated may be seen in Appendix 1. Predictive orders included were categorized by: medication, ventilation, activity, laboratory, diet, foreign body and ECMO. Predictive power of orders, defined as their parameter estimates absolute magnitude and significance (p value<0.05), were associated with frequency of occurrence. Predictive power diminished as forecast horizon increased, as illustrated in FIG. 9. Size and shading of dots reflect the magnitude and direction of discrete-time logistic regression parameter estimates. Dots for the 6 hour (i.e., leftmost) interval correspond to order parameter estimates in Table 2.

TABLE 2

Forecast model for odds of remaining in the PICU for next 6 hour horizon

| Category | Predictor Variable | OR (95% CI) | p value |
|---|---|---|---|
| Age | Age | 0.98 (0.97-0.99) | <.001 |
| Source | OR: Reference | — | — |
|  | ED | 1.53 (1.35-1.74) | <.001 |
|  | Intra-Hospital | 1.72 (1.48-2.00) | <.001 |
|  | Direct Admit | 1.42 (1.24-1.70) | <.001 |
| Readmission | Readmission Status | 1.45 (1.22-1.74) | <.001 |
| Timing | Long-Stay (LOS > 3 days) | 1.52 (1.37-1.69) | <.001 |
|  | Monday: Reference | — | — |
|  | Tuesday | 1.02 (0.83-1.25) | .850 |
|  | Wednesday | 0.77 (0.64-0.93) | .008 |
|  | Thursday | 0.77 (0.64-0.93) | .007 |
|  | Friday | 0.81 (0.67-0.98) | .028 |
|  | Saturday | 0.87 (0.72-1.06) | .163 |
|  | Sunday | 0.94 (0.77-1.14) | .524 |
|  | 6 am-Noon: Reference | — | — |
|  | Noon-6 pm | 0.23 (0.20-0.26) | <.001 |
|  | 6 pm-Midnight | 0.54 (0.46-0.62) | <.001 |
|  | Midnight-6 am | 3.70 (2.8-4.8) | <.001 |
| Medication | Enteral Count [a] | 0.91 (0.85-0.98) | .016 |
|  | Infusion Count [b] | 2.38 (1.92-2.97) | <.001 |
|  | Injection Count [c] | 1.45 (1.34-1.58) | <.001 |
| Ventilation | Continuous | 10.66 (6.25-18.17) | <.001 |
|  | BIPAP/CPAP, Continuous | 7.50 (3.98-14.13) | <.001 |
|  | BIPAP/CPAP, Nightly | 2.09 (1.34-3.25) | <.001 |
| Activity | Activity Age Appropriate | 0.23 (0.20-0.28) | <.001 |
|  | Out of Bed | 0.32 (0.25-0.42) | <.001 |
| Laboratory | APTT/D-Dimer (freq < 6 hrs) | 11.63 (5.45-10.02) | <.001 |
|  | APTT/D-Dimer (freq ≥ 6 hrs) | 4.19 (2.39-7.35) | <.001 |
|  | Lactic Acid Lab | 10.46 (4.93-22.21) | <.001 |
| Diet | Clear Liquid Diet | 1.83 (1.38-2.41) | <.001 |
|  | Formula/Human Milk | 0.67 (0.52-0.87) | .002 |
|  | Withhold Food (NPO) | 2.24 (1.74-2.88) | <.001 |
|  | Regular Diet | 0.61 (0.51-0.74) | <.001 |
| Foreign Body | Peripheral Line | 0.67 (0.57-0.81) | <.001 |
| ECMO | ECMO [d] | — | — |

[a] Enteral medication count range: None = 0, Low = 1 to 4, High > 4
[b] Infusion medication count range: None = 0, Low = 1 to 2, High > 2
[c] Injection medication count range: None = 0, Low = 1 to 9, High > 9
[d] ECMO orders supersede joint-forecast model when present Fixed variables for patients' age, admission source, and readmission status were predictive and significant through all model intervals. Temporal variables characterizing long stay patients and time-of-day were similarly significant. Time-of-day estimates demonstrate the much higher likelihood of discharge between noon and 6 pm compared to other times. Bounded medication counts by administration method were most effective in predicting LOS compared to grouping medications by type. Ventilation orders for: (1) continuous ventilation, (2) bi-level or continuous positive airway pressure (BIPAP/CPAP), and (3) nightly BIPAP/CPAP were highly predictive of remaining in the PICU. Activity orders allowing patients increased mobility were indicative of a patient becoming ready for discharge. The APTT/D-Dimer laboratory grouped orders were significant and their frequency (i.e., time from last APTT/D-Dimer lab) distinguishable. Mutually exclusive diet orders for NPO and clear liquid decreased likelihood of discharge, while formula/human milk and regular diet orders predicted an increased likelihood. Peripheral line associated orders had a low predictive power, but significantly indicate an increased rate of discharge throughout the forecast horizon. ECMO orders did not demonstrate predictive power because of scarcity, occurring in only 1.1% of patients. However, ECMO orders where highly indicative of remaining in the PICU for this population. If an ECMO associated order was present, the estimated forecast is superseded by the empirical estimate for this population. The ECMO cumulative empirical estimate was linear ranging from a 0% probability of discharge within 6 hours to a 10% chance by 3 days. In this fashion the model is adaptable to orders that are scarce, but are known to be highly predictive.

Figure 10B:
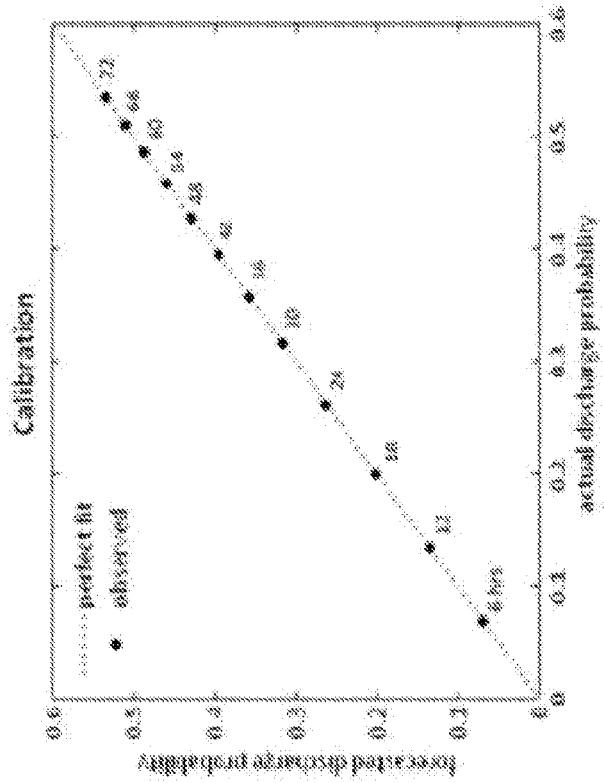
FIG. 10B illustrates a graphical view of a model forecast calibration tool, according to an embodiment of the invention.
Figure 10A:
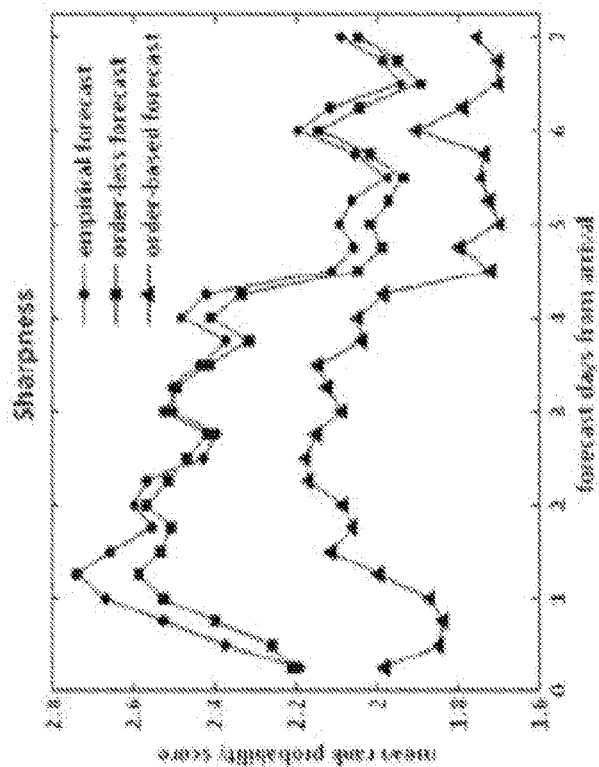
FIG. 10A illustrates a graphical view of RPS scores according to an embodiment of the invention.

Provider orders were predictive of LOS in real-time improving forecast accuracy (i.e., mean RPS) by 33% across all patients, 42% for short stay patients (<2 days), and 30% for long stay patients compared to empirical estimates. Corresponding order-based forecast accuracy was improved by 30%, 39%, and 27%, respectively compared to models using fixed and temporal predictors (i.e., order-less forecast). Mean RPS scores for all forecast windows for the order-based, empirical, and order-less forecasts were compared over the course of patients' LOS as seen by the sharpness plot in FIG. 10A. Marked improvements early in patients' LOS were observed because variation in rate of discharge (i.e., 50% patients discharged by 40.3 hours) was highest. Orders were effective in accounting for this variation. Later in patients LOS the rate of discharge declines making empirical estimates more accurate. However, the order-based model still outperforms, keying on orders indicative of discharge. The order-based model forecast calibration curve across all sliding window forecasts are illustrated in FIG. 10B. The model was well calibrated demonstrating correspondence between mean forecasted and observed discharge probability throughout the forecast horizon. Predictive performance and parameter estimates remained stable through all cross-validation procedures.

Results suggest that provider orders are useful for real-time prediction of patients'LOS. Orders directly represent provider decision making over time. This capture's a portion of information related to patients' changing conditions, making it useful for prediction. Using provider orders for real-time analysis and application is advantageous. First, all information is likely available in real-time with timestamps through a single CPOE data source. Comparatively, collecting physiological information from multiple data sources (i.e., electronic medical records, laboratory, radiology) offers more complex data management challenges. Second, orders are naturally generated requiring no user input from providers. In busy healthcare environments, applications designed for minimal maintenance are more likely to succeed. Last, the methods were designed to be generalized to other ICUs and inpatient settings despite varying order patterns and timing of work processes. Models are adaptable in that predictive orders and their parameter estimates may differ, but orders in most settings provide valuable LOS information.

Probabilistic forecasts were well-suited for the task of generating a forecast of LOS data given the variability associated with patients' conditions and hospital work processes. Probability forecasts also allow for easy aggregation and determination of bed availability. For example if 5 patients each have a 20% chance of being discharged between 12 and 18 hours, 2 beds are likely to become available during that future time interval.

Provider orders reflect dynamic changes in patients' conditions making them useful for real-time LOS prediction. This study demonstrates the development and evaluation of a continuously updated LOS forecast model driven by computerized provider orders. Providing accurate and timely LOS forecasts to key personnel may support improved management of patient flow through ICUs and hospitals. Deploying systems engineering tools as informatics applications provides the ability to leverage naturally generated clinical information to perform more evidence based management of ICU resources.

While this method has been described for use in a pediatric intensive care unit, it need not be limited to this application and could be used for any hospital or clinic unit that needed to forecast future demand. The method can also be used for any other suitable use known to one of skill in the art. The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method of forecasting a demand for a particular hospital unit comprising:
   programming a computer readable medium with steps comprising:
   logging a total number of beds in the particular hospital unit and available nursing slots to determine a capacity for the particular hospital unit;
   analyzing data for patients scheduled to stay in the particular hospital unit to predict stochastic arrivals in order to estimate a total inflow;
   predicting a length of stay of a patient in the particular hospital unit using a survival analysis based on physician orders to estimate a total outflow; and
   executing an algorithm designed to use the capacity, total inflow, and total outflow to determine the demand for the particular hospital unit.

2. The method of claim 1 wherein estimating total inflow further comprises analyzing predictive data related to a time of the day for the demand for the particular hospital unit.

3. The method of claim 1 wherein estimating total inflow further comprises analyzing predictive data related to a season of a year for the demand for the particular hospital unit.

4. The method of claim 1 wherein estimating total outflow further comprises analyzing predictive data related to the ages of patients currently staying in the particular hospital unit.

5. The method of claim 1 wherein estimating total outflow further comprises analyzing predictive data related to a source of arrival of patients currently staying in the particular hospital unit.

6. The method of claim 1 wherein estimating total outflow further comprises analyzing predictive data related to a time of the day for determining the demand for the particular hospital unit.

7. The method of claim 1 further comprising determining the demand for the particular hospital in six hour intervals.

8. The method of claim 1 further comprising determining the demand for the particular hospital unit for a 72 hour period of time.

9. The method of claim 8 further comprising determining the demand for the particular hospital unit every six hours within the 72 hour period of time.

10. The method of claim 1 further comprising predicting the stochastic arrivals using a feedback mechanism whereby the probability of stochastic arrivals being admitted to the particular hospital unit is a function of difference between forecasted demand and available capacity.

11. The method of claim 1 further comprising using a Poisson regression to model the relationship between arrival counts and predictor variables from a stochastic source.

12. The method of claim 1 further comprising executing the survival analysis using one chosen from the group consisting of discrete-time logistic regression, semi-parametric hazard regression, and parametric unbiased, stable estimates.

13. The method of claim 1 further comprising grouping the physician orders as medication orders, breathing support orders, and feed orders.

14. The method of claim 1 further comprising using physiological measures from the patient as a predictor of length of stay.

15. The method of claim 1 further comprising basing the available nursing slots on predictive data generated every 12 hours.

16. The method of claim 15 further comprising updating the available nursing slots every three hours based on trigger events.

17. The method of claim 1 further comprising grouping the length of stay as a short stay of less than three days or a long stay of more than three days.

18. The method of claim 1 further comprising updating the demand for a particular hospital unit in real time.

19. The method of claim 1 further comprising defining the particular hospital unit as a Pediatric Intensive Care Unit.

20. The method of claim 1 further comprising outputting information representative of the demand for a particular hospital unit.

* * * * *